United States Patent [19]

Cerini

[11] Patent Number: 4,537,769

[45] Date of Patent: Aug. 27, 1985

[54] STABILIZATION OF INFLUENZA VIRUS VACCINE

[75] Inventor: Costantino P. Cerini, Pearl River, N.Y.

[73] Assignee: American Cyanamid Company, Stamford, Conn.

[21] Appl. No.: 366,296

[22] Filed: Apr. 6, 1982

[51] Int. Cl.³ ............................................. A61K 39/145
[52] U.S. Cl. ........................................ 424/89; 514/7; 514/400; 514/419; 514/567; 514/574; 514/578
[58] Field of Search ........................................... 424/89

[56] References Cited

U.S. PATENT DOCUMENTS

| | | | |
|---|---|---|---|
| 3,143,470 | 8/1964 | Wilner | 424/89 |
| 3,156,620 | 11/1964 | Sharpless | 424/89 |
| 3,322,632 | 5/1967 | Schwick et al. | 435/1 |
| 3,422,188 | 1/1969 | Cabasso | 424/89 |
| 3,585,266 | 6/1971 | Emery | 424/89 |
| 3,629,399 | 12/1971 | Mauler et al. | 424/89 |
| 3,674,862 | 7/1972 | Lavender | 424/89 |
| 3,783,098 | 1/1974 | Calnek et al. | 424/89 |
| 3,937,812 | 2/1976 | Bittle et al. | 424/89 |
| 3,944,469 | 3/1976 | Bittle et al. | 424/89 |
| 3,961,046 | 6/1976 | Cerini | 424/89 |
| 4,009,258 | 2/1977 | Kilbourne | 424/89 |
| 4,029,763 | 6/1977 | Kilbourne | 424/89 |
| 4,040,904 | 8/1977 | Slater | 424/89 |
| 4,058,598 | 11/1977 | Stern et al. | 424/89 |
| 4,132,775 | 1/1979 | Volenec et al. | 424/89 |
| 4,136,168 | 1/1979 | Fontanges | 424/89 |
| 4,147,772 | 4/1979 | McAleer et al. | 424/89 |
| 4,195,076 | 3/1980 | Fontanges | 424/89 |
| 4,273,762 | 6/1981 | McAleer et al. | 424/89 |
| 4,287,178 | 9/1981 | Bittle | 424/89 |
| 4,338,335 | 7/1982 | McAleer et al. | 424/89 |
| 4,500,512 | 2/1985 | Barme | 424/89 |

OTHER PUBLICATIONS

Taguchi, H., Japan 73 10,523, (4/73), Chem. Abstr., vol. 80, 41031f, (1974).
Koyama, K., Japan 73 48,621, (7/73), Chem. Abstr., vol. 79, 108051n, (1973).
Yamashita, T., Japan 74 20,322, (2/74), Chem. Abstr., vol. 81, 54425h, (1974).
Davis et al., *Microbiology*, 3rd ed., Harper and Row, Hagerstown, Md., 1980, pp. 873 and 1121.

*Primary Examiner*—Shep K. Rose
*Attorney, Agent, or Firm*—Mary-Ellen Timbers

[57] ABSTRACT

This invention concerns stabilized influenza virus vaccines and a method of stabilizing influenza viruses and vaccines by the addition of protein hydrolysates and/or amino acids.

21 Claims, No Drawings

STABILIZATION OF INFLUENZA VIRUS VACCINE

BACKGROUND OF THE INVENTION

A number of vaccines are currently available or noted in the literature which confer either complete or partial immunity to influenza virus infection by inducing the production of protective antibodies which are active against the viral surface antigens, the proteins hemagglutinin and neuraminidase.

Complete immunity may be understood to be that conferred by conventional vaccines consisting of whole or disrupted virus particles containing those antigens in varying degrees of purification which generate antibodies which block the replication of invading virus particles and thereby prevent the occurrence of disease.

Partial immunity may be understood to be that conferred by vaccines containing those antigens of virus particles, in varying degrees of purification, which allow replication of invading virus particles yet restrict the disease to a substantially asymptomatic process resulting in the establishment of natural immunity.

The stimulation of antibody production, or immunogenicity of the neuraminidase antigen of influenza vaccine virus is considered to be a minor component in the establishment of complete immunity, but the major factor in establishing a state of partial immunity. See *J. Infect. Diseases*, 140, 844 (1977). Influenza vaccines have recently been prepared which incorporate isolated neuraminidase antigen as the sole active component. See U.S. Pat. Nos 4,029,763 and 4,136,168.

The immunogenicity of the neuraminidase antigen has been found to closely parallel the enzymatic activity of the neuraminidase molecule. The stability of this activity will affect storage life of the vaccine. This is particularly true of influenza virus vaccines of neuraminidase Type 1 which are very labile at 4° C. storage temperatures. Our tests have indicated that such influenza virus vaccines stored at 4° C. lost almost all detectable neuraminidase enzyme activity after approximately 2 to 3 months. This brief storage life has caused obvious problems in the distribution of vaccine and has hampered attempts to calculate the actual effective immunogenic dose. See, D. Bucher and D. Palese, The Biologically Active Protein of Influenza Virus: Neuraminidase, in *The Influenza Viruses and Influenza* (E. D. Kilbourne, Ed.), Academic Press, N.Y. (1975), at page 93.

Casein hydrolysates (digests) have been employed as one component of vaccine-stabilizing media and have been used to enhance the growth of rabies virus. For example, U.S. Pat. No. 4,147,772 discloses a stabilized vaccine consisting of an activated or attenuated virus, partially hydrolyzed gelatin, a polyhydric alcohol and a buffered acidic medium.

U.S. Pat. No. 3,783,098 discloses stabilization of cell-free Group B Herpes virus suspensions during extraction and lyophilization with skim milk or casein and an amine, which may be an enzymatic digest of milk protein.

U.S. Pat. No. 3,629,399 discloses an orally-administrable polio vaccine comprising an attenuated virus stabilized with phosphate buffer, casein, and casein hydrolysate.

U.S. Pat. No. 3,143,470 discloses a process for the production of a live rabies virus in a medium containing at least 0.3% by weight of pancreatic digest of casein.

It has been discovered that a casein hydrolysate such as N-Z AMINE ® NAK or N-Z AMINE ® A, (Sheffield Products, Memphis, Tennessee) or simpler amino acids will effectively stabilize the neuraminidase activity of stored influenza vaccines, resulting in an enhanced effective period of usefulness of such vaccines.

BRIEF DESCRIPTION OF THE INVENTION

It is an object of this invention to provide a method to preserve the immunogenic capability of vaccines containing neuraminidase at as high a value as possible for as long as possible during storage. Such stabilized vaccines retain substantially original capabilities for 10 to 20 times longer than is achieved by unpreserved vaccines of the same type.

It is further object of this invention to provide a method to maintain the immunogenic level of neuraminidase at a nearly constant level over a long period of time.

Stabilized neuraminidase containing vaccines are also within the scope of this invention.

It has now been discovered that storing influenza virus vaccine in the presence of protein hydrolysates, amino acids, and combinations thereof greatly increases the useful storage life of the vaccines. Preferred vaccines include influenza virus vaccines and preferred protein hydrolysates include a pancreatic digest of casein and the like. An especially preferred protein hydrolysate is N-Z AMINE ® NAK or N-Z AMINE ® A. In particular the immunogenic response caused by the neuraminidase antigen preserved according to this invention has been found to remain elevated over a much longer period of time. The immunogenic response, as measured with reference to neuraminidase enzymatic activity, is maintained at substantially the original value for a much longer period than is achieved by unpreserved antigen. In a preferred form of preserved vaccine, the response substantially remains close to original values for 10–20 times longer than the response caused by unpreserved antigen. The method of the present invention is applicable to purified neuraminidase or to vaccines of both bi- and monospecific immunigenicity for the stimulation of either complete or partial immunity. As referred to herein, a monospecific vaccine is one which stimulates production of antibodies effective against neuraminidase antigens, while a bispecific vaccine induces antibodies that interact immunogenically with both viral surface antigens.

DETAILED DESCRIPTION OF THE INVENTION

The present invention is directed to a stabilized neuraminidase containing vaccine in lyophilized or liquid form, and a stabilizing agent which may be a protein hydrolysate, an amino acid or mixtures thereof; and to methods for preparing such vaccines.

The protein hydrolysates of this invention are derived from proteins such as conjugated proteins, a general example of which is the group known as phosphoproteins, and a specific example of which is the glycophosphoproteins.

A preferred protein hydrolysate of the glycophosphoproteins is a pancreatic digest of casein, preferably N-Z AMINE ® NAK or N-Z AMINE ® A. The typical analysis of N-Z AMINE ® NAK is as follows:

| Analysis | |
|---|---|
| Moisture | 3.5% |
| Total Nitrogen | 12.1% |
| Free Amino N/Total N | 51.4% |
| Potassium | 1.25% |
| Sodium | 1.75% |
| pH (2% solution) | 6.7 |
| Solubility (clear, 30° C.) | 25 g /1000 cc |

| Amino Acid Assay | | | |
|---|---|---|---|
| Lysine | 69.8 mg/g | Alanine | 28.4 |
| Histidine | 23.3 | Cystine | Not calculable |
| Arginine | 27.6 | Valine | 60.4 |
| Aspartic Acid | 66.1 | Methionine | 24.6 |
| Threonine | 38.8 | Isoleucine | 46.4 |
| Serine | 50.4 | Leucine | 75.8 |
| Glutamic Acid | 181.0 | Tyrosine | 29.7 |
| Proline | 89.6 | Phenylalanine | 40.7 |
| Glycine | 17.6 | Tryptophan | 10.4 |

The analysis of N-Z AMINE ® A is similar, except that potassium salts are absent.

A slight variation in these parameters may occur from lot to lot and will not materially reduce the effectiveness of the digest.

The amino acids which are effective in the present invention are selected from the group consisting of the naturally-occurring alpha-amino acids, preferably alanine, aspartic acid, glycine, leucine, lysine, histidine, methionine, phenylalanine, proline, serine, threonine, tryptophan, valine or mixtures of any two or more of these amino acids. Generally, any natural or synthetic amino acid or lower molecular weight peptide which inhibits loss of neuraminidase activity in the vaccine to be stabilized may be used The vaccines which may be effectively stabilized by the method of the present invention include all those containing viral neuraminidase as either a component of a whole virus incorporated within the vaccine or in an isolated and purified form. Both mono and bispecific influenza virus vaccines may be stabilized by the method of the present invention and include, for example, the recombinant X-49 virus vaccine of H3N2 type [(A/Eng/865/75)R], type H1N1 (A/USSR/92/77), or the recombinant X-68 vaccine of H7N1 type [A/Equine/Prague/56(H7)-A/USSR/92/77(N1)R].

Influenza vaccines containing purified neuraminidase which may be stabilized by the method of this invention include those containing Type N1 neuraminidase or Type N2 neuraminidase. The neuraminidase component of these vaccines may be obtained by various methods (i.e., U.S. Pat. No. 4,136,168 which is incorporated herein by reference) from strains of *Myxovirus Influenza* such as Hong Kong virus $A_{2/68}(H_3N_2)$, the NWS strain of virus $A_0$, mutant of strain RI/5+ of virus, strain $A_3$-XL of the virus $A_2$, human $A_2$ virus/Singapore/1/57, the virus $A_2$/England/52/64, the virus $A_2$/England/76/66, the recombinant X-7(F-1), or the like.

The proportion of protein hydrolysates, amino acids or mixtures thereof, to be incorporated in the virus products for stabilizing purposes is subject to variation depending on the concentration of the vaccine, the relative lability of the neuraminidase antigen present and other similar factors. Conveniently, the protein hydrolysates, amino acids or mixtures thereof in the form of a dry powder or dilute aqueous solution prepared in water or standard phosphate-buffered vaccine diluents, are incorporated in the fluid virus material with thorough mixing at low or ambient temperature to obtain a homogenous suspension or solution. In general, a concentration of at least about 1.0% (w./v.) is preferred. For maximum stability, a total concentration of 4.0% (w./v.) is employed. Concentrations as low as about 0.01% (w./v.) may also be satisfactory. The invention contemplates the use of higher concentrations.

The invention as indicated contemplates not only fluid, aqueous virus materials, but also dry, nonaqueous products such as may be prepared by drying the mentioned fluid products. Using the methods of this invention, fluid, stabilized, monospecific N1 influenza vaccines may be stored at about 4° C. for at least 5 months with retention of at least about 80% of their initial activity; fluid, stabilized bispecific N1 influenza vaccines may be stored at about 4° C. for at least 9 months with retention of at least about 75% of their original activity; and stabilized bispecific N2 influenza vaccines may be stored for 24 hours at about 37° C. with retention of at least 70% of their original activity. Stabilized, purified neuraminidase vaccines would be expected to exhibit similar stabilities.

In accordance with the conventional practice, the products of the invention are desirably processed under aseptic conditions using components which preliminarily have been rendered bacterially sterile. Sterility on storage can be maintained by incorporation of an antigen-compatible germicidal substance such as thimerosal. Unless otherwise indicated herein, the antigenic substances are preferably kept cold (about 4° C.) where possible during treatment.

The stabilized vaccines obtained according to the method of this invention are presented in the form of pharmaceutical preparations, more particularly liquid preparations suitable for parenteral intranasal or oral administration. A preferable form of administration is via intramuscular inoculation.

The usual dosage depends on the age or weight of the patient and the number of administrations per day, as determined in accordance with the judgement of the administering phyician. The preferred doses are suggested in package literature and are determined from dose response studies in human trials and in accordance with the requirements of the Bureau of Biologics, U.S. Food and Drug Administration.

The invention will be further described by reference to the following examples setting forth in detail several preferred embodiments of the inventive concept as well as comparisons to vaccines presently used of lesser stability.

The following examples illustrate the present invention without, however, limiting the same thereto. Other examples of this invention will be apparent to those skilled in the art without departing from the spirit of the invention.

EXAMPLE 1

STABILIZATION OF MONOSPECIFIC TYPE N1 VIRUS VACCINE

Table I shows the effect of N-Z AMINE ® NAK on the stabilization of the immunogenic response as measured by neuraminidase activity of monospecific recombinant antigenically hybridized X-68 influenza virus vaccine of H7N1 type [A/Equine/Prague/56(H7)-A/USSR/92/77(N1)R].

A 960 ml sample of H7N1 bulk vaccine was divided into two portions of 900 ml and 60 ml. A 47.4 ml portion of a 20% solution of N-Z AMINE ® NAK prepared in vaccine diluent, and 0.9 ml of an 11.8% solution of thimerosal prepared in water were added to the 900 ml portion. The 60 ml portion received 3.2 ml of vaccine diluent and 0.6 ml of 11.8% thimerosal solution. Both portions were sterilized by filtration and stored at 4° to 8° C. in bulk form. Periodically samples were aseptically removed and assayed for neuraminidase activity using a modification of the Warren-Aminoff Method (Webster, R. G. and Laver, W. G., J. Immunol., 99, 49–54 (1967)).

Values obtained by assaying thawed 0.3 ml portions of a preparation sealed in glass ampules of a neuraminidase control stored at −70° C. are also given. Table I presents the results of these tests.

TABLE I

Stabilization of H7N1 Vaccine at 4° C. by Addition of N—Z—AMINE ® NAK

| Days at 4° C. | H7N1 Vaccine with N—Z—AMINE ® NAK | H7N1 Vaccine without N—Z—AMINE ® NAK | H7N1 Frozen Control |
| --- | --- | --- | --- |
| 0 | 36.3* | 34.0 | 45.8 |
| 6 | 37.7 | 26.8 | 46.2 |
| 12 | 33.2 | 18.5 | 44.3 |
| 13 | 28.1 | 17.8 | 38.2 |
| 21 | 34.8 | 16.9 | 45.7 |
| 26 | 35.2 | 12.5 | 47.9 |
| 41 | 39.1 | 10.4 | 46.9 |
| 47 | 46.0 | 6.1 | 47.6 |
| 55 | 44.1 | 4.3 | 50.4 |
| 79 | 34.4 | 0.5 | 49.0 |
| 90 | 32.1 | 0.9 | 47.2 |
| 105 | 27.0 | 0.7 | 41.6 |
| 128 | 31.8 | 0.3 | 49.1 |
| 161 | 28.9 | 0.1 | 48.9 |

*Number of nanomoles of N—Acetyl neuraminic acid released from fetuin per minute per milliter of vaccine.
The stabilized vaccine lost approximately 20% of its activity over a 5-month period while the vaccine prepared without stabilizer lost essentially all of its activity in three months.

EXAMPLE 2

STABILIZATION OF BISPECIFIC TYPE N1 VIRUS VACCINE

A 173 ml portion of H1N1 (A/USSR/92/77) bulk vaccine was divided into two aliquots of 86.5 ml each. To one aliquot, 4.6 ml of a 20% solution of N-Z AMINE ® NAK prepared in vaccine diluent, and 0.09 ml of an 11.8% solution of thimerosal in water were added. The other aliquot received 4.6 ml of vaccine diluent and 0.09 ml of an 11.8% thimerosal solution. Both aliquots were sterilized by filtration and stored in bulk at 4° C. to 8° C. Samples were aseptically removed and monitored for neuraminidase enzyme activity over a period of approximately 9 months by the procedure of Example 1. Table II presents the results of these tests.

TABLE II

Stabilization of H1N1 Influenza Vaccine at 4° C. by Addition of N—Z—AMINE ® NAK

| Days at 4° C. | H1N1 Vaccine with N—Z—AMINE ® NAK | H1N1 Vaccine without N—Z—AMINE ® NAK | H7N1 Frozen Control |
| --- | --- | --- | --- |
| 0 | 56.0** | 22.5 | 49.0 |
| 11 | 56.2 | 11.2 | 47.2 |
| 26 | 50.2 | 6.8 | 41.4 |
| 83 | 56.4 | 0.6 | 48.9 |

TABLE II-continued

Stabilization of H1N1 Influenza Vaccine at 4° C. by Addition of N—Z—AMINE ® NAK

| Days at 4° C. | H1N1 Vaccine with N—Z—AMINE ® NAK | H1N1 Vaccine without N—Z—AMINE ® NAK | H7N1 Frozen Control |
| --- | --- | --- | --- |
| 279 | 42.0 | 0.0 | 32.0* |

*New lot of frozen control used.
**Number of nanomoles of N—acetyl neuraminic acid (NANA) released from fetuin per minute per milliliter of vaccine.

The stabilized vaccine lost approximately 25% of its original activity over a 9-month period while the vaccine prepared without stabilizer lost essentially all of its activity over a 3-month period.

EXAMPLE 3

STABILIZATION OF A BISPECIFIC TYPE N2 VIRUS VACCINE

Type N2 neuraminidase is stable at 4° C. Accelerated stability studies at 37° C. were employed to demonstrate the effect of N-Z AMINE ® NAK on type N2 neuraminidase containing vaccines.

A 40 ml sample of a bispecific high yielding recombinant X-49 influenza virus vaccine of H3N2 type [(A/Eng/864/75)R] was divided into two 19 ml aliquots. One aliquot received 1 ml of a 20% solution of N-Z AMINE ® NAK in vaccine diluent. The other aliquot received 1 ml of vaccine diluent. Ten ml were removed from each aliquot and held at 37° C. for 24 hours while the remaining portion was stored at 4° C. At the end of the 24 hour incubation period all samples were assayed for neuraminidase enzyme activity by the procedure of Example 1. An assay performed on a control sample of known activity was used to check the assay procedure. Table III presents the results obtained.

TABLE III

Stabilization of H3N2 Influenza Vaccine at 37° C. by Addition of N—Z—AMINE ® NAK

| Time at 37° C. | H3N2 Vaccine with N—Z—AMINE ® NAK | H3N2 Vaccine without N—Z—AMINE ® NAK | H6N1 Frozen Control |
| --- | --- | --- | --- |
| 0 | 192* | 193 | 31 |
| 24 Hrs. | 135 | 73 | — |

*Number of nanomoles of NANA released from fetuin/minute/ml of vaccine.

These results indicate that in accelerated stability studies at 37°, stabilized X-49 (H3N2) influenza virus lost 30% of its original enzyme activity, while the non-stabilized virus lost 62% of its original activity over a 24-hour period.

EXAMPLE 4

STABILIZATION OF VACCINE IMMUNOGENICITY

A. Stability of Vaccine Immunogenicity After Incubation at 4° C.

A bulk preparation of monospecific X-68 influenza virus vaccine of H7N1 Type [A/Equine/Prague/56(H7)-A/USSR/97/77/(N1)R] containing 855 ml was formulated. A 60 ml sample of this preparation was removed, filtered and stored at 4° to 8° C. To the remaining 790 ml was added 41.6 ml of 20% N-Z AMINE ® NAK in vaccine diluent. This vaccine bulk was filtered, distributed into syringes, and held at 4° to 8° C.

After 144 days of storage the vaccine sample taken prior to the addition of N-Z AMINE ® NAK was compared to the vaccine containing N-Z AMINE ® NAK in 16 rabbits.

Vaccine without N-Z AMINE ® NAK was tested undiluted and at dilutions of 1:4 and 1:16. Vaccine with N-Z AMINE ® NAK was tested undiluted and at dilutions of 1:4, 1:16, 1:64, and 1:128. Each dilution (0.5 ml) was inoculated intravenously into two rabbits at day 0 and at day 40. Rabbits were bled at days 0, 10, 21, 40 and 47. Sera from these bleedings were tested for the development of antibody to neuraminidase type N1 by a neuraminidase inhibition test. (Center for Disease Control. 1975. Advanced Laboratory Techniques For Influenza Diagnosis. Immunology Series No. 6. Center For Disease Control, Atlanta, Ga.) Sera which showed antibody titers of ≧1:3.2 were considered positive for the presence of serum neuraminidase inhibiting antibody. The dilution of vaccine at which 50% of the rabbits tested showed a positive response is presented in Table IV.

TABLE IV

Rabbit Antigenicity of H7N1 Recombinant Vaccines With and Without N—Z—AMINE ® NAK After 4° C. Storage for 144 Days

| H7N1 Vaccine | Enzyme Activity (nm/ml/min) | Day of Bleeding | | | | |
|---|---|---|---|---|---|---|
| | | 0* | 10 | 21 | 40* | 47 |
| With N—Z—AMINE ® NAK | 26.2 | 0 | 0 | Undilute** | 1:2 | 1:64 |
| Without N—Z—AMINE ® NAK | ≦6.5 | 0 | 0 | 0 | 0 | 1:4 |

*2 rabbits per dilution inoculated with vaccine at 0 and 40 days.
**Dilution of vaccine at which 50% of inoculated rabbits show a positive antibody response.

These results indicate that the stabilized vaccine with a neuraminidase enzyme activity of approximately 26 units (nanomoles/ml/min) is capable of stimulating a primary antibody response in rabbits where a nonstabilized aliquot with less than 6 units of activity is not. The secondary or booster response following the second inoculation is 16 fold higher after inoculation with stabilized vaccine than after inoculation with the nonstabilized aliquot.

B. Stability of Vaccine Immunogenicity After Incubation at 37° C.

From a 78 ml sample of monospecific X-68 influenza virus vaccine of H7N1 Type [A/Equine/Prague/56(H7)-A/USSR/97/77(N1)R], two 19 ml aliquots were prepared. One aliquot received 1 ml of a 20% solution of N-Z AMINE ® NAK in vaccine diluent. The other aliquot received 1 ml of vaccine diluent. A 10 ml portion was removed from each aliquot and held at 37° C. for 22 hours. At the end of the 22 hour incubation period both samples were assayed for neuraminidase activity by the procedure of Example 1, stored for 24 hours at 4° C. and tested for antibody response in rabbits by the procedures used in Part A, above. Results are presented in Table V.

TABLE V

Rabbit Antigenicity of H7N1 Recombinant Vaccines With and Without N—Z—AMINE ® NAK After 37° C. Incubation for 22 Hrs.

| H7N1 Vaccine | Enzyme Activity (nm/ml/min) | Day of Bleeding | | | | |
|---|---|---|---|---|---|---|
| | | 0* | 10 | 21 | 40* | 47 |
| With N—Z—AMINE ® NAK | 31 | 0 | 0 | 1:2** | 1:4 | 1:32 |
| Without N—Z—AMINE ® NAK | ≦5 | 0 | 0 | 0 | 0 | 1:2 |

*2 rabbits per dilution inoculated with vaccine at 0 and 40 days.
**Dilution of vaccine at which 50% of inoculated rabbits show a positive antibody response.

These results reproduce the observation that vaccine containing more neuraminidase enzyme activity (31 units) is more immunogenic in terms of rabbit primary and booster responses than vaccine with less activity (5 units). A primary response is seen only with the stabilized vaccine, and the booster response is again 16 fold higher than the nonstabilized aliquot of vaccine.

EXAMPLE 5

STABILIZATION OF VACCINES WITH AMINO ACIDS

Sixteen amino acids which are typically found in analyses of N-Z AMINE ® NAK were tested for stabilizing activity. Each was used at the concentration found in a typical total amino acid assay of a one percent solution of the hydrolysate.

A 75 ml portion of monospecific X-68 influenza virus vaccine of H7N1 Type [A/Equine/Prague/56(H7)-A/USSR/97/77(N1)R] was divided into 19 aliquots of 3.8 ml. Sixteen of these aliquots were used to prepare samples containing a concentration of each amino acid similar to the concentration one would expect in a 1% solution of N-Z AMINE ® NAK based on a typical amino acid analysis. This was done by adding 0.2 ml of a stock amino acid solution to each aliquot. Two aliquots were also prepared with and without N-Z AMINE ® NAK. These eighteen samples were incubated at 37° C. for 24 hours. The 19th aliquot of vaccine was kept at 4° C. as a control. At the end of the 24 hour incubation period all samples were assayed for neuraminidase enzyme activity by the procedure of Example 1. Table VI lists the activities found for each amino acid at the concentration tested.

TABLE VI

Stabilization of H7N1 Neuraminidase Enzyme Activity at 37° C. by Various Amino Acids

| Additive | Temp. of Incubation | Conc. | Units of Activity* |
|---|---|---|---|
| Alanine | 37° C. | .03% | 9.0 |
| Aspartic Acid | " | .07% | 5.9 |
| Glutamic Acid | " | .18% | 4.5 |

TABLE VI-continued

Stabilization of H7N1 Neuraminidase Enzyme
Activity at 37° C. by Various Amino Acids

| Additive | Temp. of Incubation | Conc. | Units of Activity* |
|---|---|---|---|
| Glycine | " | .02% | 8.5 |
| Isoleucine | " | .05% | 5.2 |
| Leucine | " | .08% | 7.3 |
| Lysine | " | .07% | 8.5 |
| Histidine | " | .02% | 13.1 |
| Methionine | " | .02% | 8.9 |
| Phenylalanine | " | .04% | 9.1 |
| Proline | " | .09% | 12.3 |
| Serine | " | .05% | 9.1 |
| Threonine | " | .04% | 6.7 |
| Tryptophan | " | .01% | 10.4 |
| Tyrosine | " | .03% | 4.4 |
| Valine | " | .06% | 6.7 |
| None | " | — | 4.8 |
| N—Z—AMINE ® NAK | " | 1.0% | 36.7 |
| None | 4° | — | 38.9 |

*Nanomoles of N—acetyl neuraminic acid released from fetuin per minute per milliter.

Table VI indicates that except in three cases, addition of a single amino acid to the influenza virus has some stabilizing effect on activity at the concentration indicated, although apparently not to the same extent as the N-Z AMINE ® NAK used as a control. Stabilization of ≦120% of the 37° C. control was considered to be significant. Higher amino acid concentrations would be expected to provide a greater stabilizing effect, as would combinations of N-Z AMINE ® NAK and amino acids.

EXAMPLE 6

STABILIZATION OF VACCINES WITH HISTIDINE AND PROLINE

Two amino acids with high stabilizing activity were selected for use at increasing concentrations and in combination with each other to measure stabilizing effect on influenza virus neuraminidase activity.

A 48 ml portion of a monospecific X-68 influenza virus vaccine of H7N1 Type [A/Equine/Prague/56(H7)-A/USSR/97/77(N1)R] was divided into 11 aliquots of 3.8 ml. To eight of these were added 0.2 ml of various stock solutions of histidine and proline to give the concentrations tested. Two aliquots were also prepared with and without N-Z AMINE ® NAK. Aliquots of 1.8 ml of the histidine and proline samples were combined to give the 4 combination of concentrations noted in Table VII. These 14 samples were incubated at 37° C. for 24 hours. An aliquot of vaccine alone was kept at 4° C. as a control. At the end of the 24 hour incubation period all samples were assayed for neuraminidase enzyme activity by the procedure of Example 1. Table VII lists the results obtained.

TABLE VII

Stabilization of H7N1 Neuraminidase Enzyme Activity at 37° C. By Amino Acids at Various Concentrations and Combinations

| No. | Histidine Concentration % w/v | Neuraminidase Activity-24 Hrs Post 37° C. | No. | Proline Concentration % w/v | Neuraminidase Activity-24 Hrs Post 37° C. | Combination of Concentration Numbers | Neuraminidase Activity-24 Hrs Post 37° C. |
|---|---|---|---|---|---|---|---|
| 1 | 0.02 | 13.0 | 5 | 0.09 | 12.3 | 1 & 5 | 17.8 |
| 2 | 0.05 | 17.3 | 6 | 0.18 | 17.5 | 2 & 6 | 23.4 |
| 3 | 0.09 | 23.8 | 7 | 0.36 | 26.2 | 3 & 7 | 32.3 |
| 4 | 0.13 | 27.9 | 8 | 0.54 | 30.7 | 4 & 8 | 35.4 |

Control Values:
Virus alone at 37° C. — Activity = 4.7
Virus with 1% N—Z AMINE ® NAK at 37° C. — Activity = 40.0
Virus alone at 4° — Activity = 46.8

Table VII demonstrates that increasing concentrations of amino acids increase the stabilizing effect, and in all cases combinations of two amino acids yielded higher values of activity than either amino acid alone.

It will be obvious to persons skilled in the art that although N-Z AMINE ® NAK is the preferred stabilizer, other protein hydrolysates and peptides, as well as amino acids alone or in various combinations and concentrations will act to stabilize neuraminidase enzyme activity.

While certain representative embodiments of the present invention have been shown for the purpose of more particularly illustrating the invention, it will be apparent to those skilled in the art that various changes and modifications may be made therein without departing from the scope and spirit of the invention.

What is claimed is:

1. In a method for stabilizing the immunogenicity of neuraminidase and neuraminidase containing antiviral influenza vaccines neuromidase-stabilizing formulating the vaccine with an effective amount within the range of about 0.0% to about 4.0% w/v of an agent selected from the group consisting of protein hydrolysates, amino acids and combinations thereof.

2. The method of claim 1 wherein the protein hydrolysates are enzymatic digests of casein.

3. The method of claim 2 wherein the protein hydrolysate is N-Z AMINE ® NAK or N-Z AMINE ® A.

4. The method of claim 3 wherein the N-Z AMINE ® NAK is present at a concentration of 0.2-4.0% by weight of the vaccine.

5. The method of claim 1 wherein the amino acids are selected from the group consisting of alanine, aspartic acid, glycine, histidine, leucine, lysine, methionine, phenylalanine, proline, serine, threonine, trytophan, valine, or mixtures thereof.

6. The method of claim 5 wherein the amino acids are histidine or proline, or mixtures thereof.

7. The method of claim 5 wherein the amino acids are present in a concentration of 0.01-4.0% by weight of the vaccine.

8. The method of claim 6 wherein the amino acids are present in a concentration of 0.01-4.0% by weight of the vaccine.

9. The method of claim 1 wherein the vaccine is a bispecific influenza vaccine selected from the group consisting of H1N1, H2N2, and N3N2.

10. The method of claim 1 wherein the vaccine is a monospecific influenza vaccine such as H7N1 or H7N2.

11. The method of claim 1 wherein the vaccine consists esssentially of purified neuraminidase of type N1 or type N2.

12. An improved influenza vaccine effective in eliciting the production of immunizing antibodies in mammals which vaccine contains viral neuraminidase, wherein the improvement consists essentially of a neuromidase stabilizer in said vaccine of a protein hydrolysate or at least one amino acid in sufficient neuromidase-stabilizing quantity within the range of about 0.0% to about 4.0% w/v to stabilize the enzymatic activity of the neuraminidase.

13. The improved vaccine as recited in claim 12 wherein the protein hydrolysate is a pancreatic digest of casein.

14. The improved vaccine as recited in claim 12 wherein the protein hydrolysate is N-Z AMINE NAK ® or N-Z AMINE A ®.

15. The improved vaccine as recited in claim 14 wherein N-Z AMINE NAK ® or N-Z AMINE A ® comprises about 0.01% to about 4.0% (w./v.).

16. The improved vaccine as recited in claim 12 wherein the amino acid is selected from the group consisting of alanine, aspartic acid, glycine, histidine, leucine, lysine, methionine, phenylalanine, proline, serine, threonine, trytophan, valine and mixtures thereof.

17. The improved vaccine as recited in claim 16 wherein the amino acid is histidine, proline or a mixture thereof.

18. The improved vaccine as recited in claim 16 wherein the amino acid comprises about 0.01% to about 4.0% (w./v.).

19. The improved vaccine as recited in claim 12 wherein the vaccine is a bispecific influenza vaccine selected from the group consisting of H1 N1, H2 N2 and H3N2 types.

20. The improved vaccine as recited in claim 12 wherein the vaccine is a monospecific influenza vaccine H7N1 or H7N2.

21. The improved vaccine as recited in claim 12 wherein the vaccine consists essentially of purified neuraminidase of type N1 or type N2.

* * * * *

UNITED STATES PATENT OFFICE
CERTIFICATE OF CORRECTION

Patent No. 4,537,769    Dated August 27, 1985

Inventor(s) Costantino P. Cerini

It is certified that error appears in the above-identified patent and that said Letters Patent are hereby corrected as shown below:

In the specification:

Col. 3, line 20, "absent" should read -- reduced --.

Col. 5, line 5, "0.6" should read -- 0.06 --.

Col. 9, line 27, "9.1" should read -- 9.2 --.

Col. 9, line 29, "9.1" should read -- 9.4 --.

In the claims:

Claim 1 should read:

-- 1. In a method for stabilizing the immunogenicity of neuraminidase and neuraminidase containing antiviral influenza vaccines the improvement consisting essentially of

UNITED STATES PATENT OFFICE
CERTIFICATE OF CORRECTION

Patent No. 4,537,769              Dated  August 27, 1985

Inventor(s) Costantino P. Cerini

It is certified that error appears in the above-identified patent and that said Letters Patent are hereby corrected as shown below:

formulating the vaccine with an effective neuraminidase-stabilizing amount within the range of about 0.0% to about 4.0% w/v of an agent selected from the group consisting of protein hydrolysates, amino acids and combinations thereof.--

Col. 10, ln. 66, in claim 9, "N3N2" should read -- H3N2 --.

Claim 12 should read:

-- 12. An improved influenza vaccine effective in eliciting the production of immunizing antibodies in mammals which vaccine contains viral neuraminidase, wherein the improvement consists essentially of a neuraminidase stabilizer in said vaccine of a protein hydroysate or at least

UNITED STATES PATENT OFFICE  Page 3 of 3
CERTIFICATE OF CORRECTION

Patent No. 4,537,769  Dated August 27, 1985

Inventor(s) Costantino P. Cerini

It is certified that error appears in the above-identified patent and that said Letters Patent are hereby corrected as shown below:

one amino acid in sufficient neuraminidase-stabilizing quantity within the range of about 0.0% to about 4.0% w/v to stabilize the enzymatic activity of the neuraminidase.--

Signed and Sealed this

Twenty-eighth Day of October, 1986

[SEAL]

Attest:

DONALD J. QUIGG

Attesting Officer   Commissioner of Patents and Trademarks